United States Patent [19]

Nguyen Mong

[11] 4,268,507

[45] May 19, 1981

[54] MONOPHOSPHONATE COMPOUNDS AS HYPOGLYCEMIC AND/OR ANTIARTHEROGENIC AGENTS

[75] Inventor: Lan Nguyen Mong, Nyon, Switzerland

[73] Assignee: Symphar S.A., Geneva, Switzerland

[21] Appl. No.: 116,809

[22] Filed: Jan. 30, 1980

[30] Foreign Application Priority Data

Feb. 13, 1979 [GB] United Kingdom ............... 04992/79

[51] Int. Cl.³ .................. A61K 31/66; C07F 9/38; C07F 9/40
[52] U.S. Cl. .................................. 424/217; 260/951; 260/961; 424/222
[58] Field of Search ............. 260/951, 961, 502.4 R; 424/217, 222

[56] References Cited

U.S. PATENT DOCUMENTS

| | | | |
|---|---|---|---|
| 3,524,846 | 8/1970 | Moffatt et al. | 260/961 |
| 4,182,759 | 1/1980 | Diana | 260/951 |

FOREIGN PATENT DOCUMENTS

| | | | |
|---|---|---|---|
| 737036 | 9/1955 | United Kingdom | 260/961 |
| 751755 | 7/1956 | United Kingdom | 260/961 |
| 777718 | 6/1957 | United Kingdom | 260/932 |
| 1366600 | 9/1974 | United Kingdom | 260/961 |
| 1470113 | 4/1977 | United Kingdom | 260/961 |

OTHER PUBLICATIONS

Kosolapoff, et al., "Organic Phosphorus Compounds", vol. 7, (1976), pp. 158, 180, & 223.

*Primary Examiner*—Anton H. Sutto
*Attorney, Agent, or Firm*—Young & Thompson

[57] ABSTRACT

This invention relates to new monophosphonate compounds of formula $X-C_6H_4-(O)_m-(CH_2)_n-R$ where R is $-PO_3Me_2$, $-PO_3Et_2$, $-PO_3H_2$ or $-PO_3Na_2$, X is a halogen, preferably chlorine, in position o, m or p, preferably in position p; m is 0 or 1; and n is 0, 1, 2, 3, 4, 5 or 6, which possess remarkable activity as hypoglycemic and/or antiatherogenic agents, and are usable in pharmaceutical compositions to alter lipoprotein profiles in favor of high density lipoproteins and to clear cholesterol from various tissues.

8 Claims, No Drawings

MONOPHOSPHONATE COMPOUNDS AS HYPOGLYCEMIC AND/OR ANTIARTHEROGENIC AGENTS

The present invention relates to new monophosphonate compounds, and more particularly to halogenophenylalkylphosphonates and to halogenophenoxyalkylphosphonates.

Some phosphorus compounds have been previously shown to demonstrate hypoglycemic activity, for example phenacyltriphenylphosphoranes and phosphonium salts as described in "J. Medicinal Chemistry" 18(9), 952 (1975). More recently, Parker et al. published on the synthetic steroid inhibitory action and alkylphosphonates and phosphonophosphates in "Biochimica et Biophysica Acta" 530, 24 (1978).

Therefore, the present inventor has undertaken investigations of new phosphono compounds and has found that halogenophenylalkylphosphonates and halogenophenoxyalkylphosphonates of formula (I) possess remarkable activity as hypoglycemic and/or antiartherogenic agents, as well as the ability to alter lipoprotein profiles in favour of high density lipoproteins, and to clear cholesterol from various tissues.

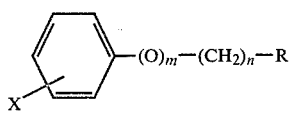

In the above formula (I), R is —PO$_3$Me$_2$, —PO$_3$Et$_2$, —PO$_3$H$_2$ or —PO$_3$Na$_2$, X is a halogen, preferably chlorine, in position o, m or p, preferably in position p; m is 0 or 1; and n is 0, 1, 2, 3, 4, 5 or 6.

The halogenophenoxyalkylphosphonate compounds of formula (Ia) and halogenophenylalkylphosphonate compounds of formula (Ib),

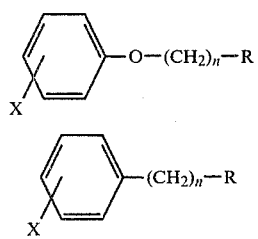

where R, n and X are as defined above, can be prepared according to the following scheme:

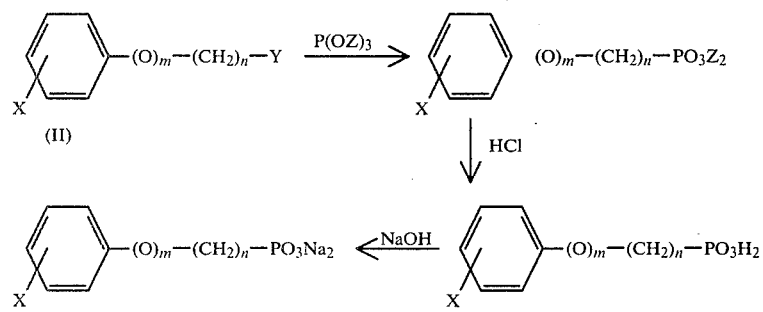

where m is 0 or 1, Y is Cl or Br and Z is Me or Et.

Starting halides of formula (II) where m=1 can be prepared according to C. S. Marvel and A. L. Tanenbaum (Organic Syntheses, Coll. Vol. I, p. 435, 1944) or to J. D. Genzer et al. (J. Am. Chem. Soc. 73, 3159, 1951).

Starting halides of formula (II) where m=0 can be prepared according to W. H. Sanders and R. A. Williams (J. Am. Chem. Soc. 79, 3712, 1957), or to R. W. Bott et al. (J. Chem. Soc. 1548, 1964), or further to H. Gilman and O. R. Marrs (J. Org. Chem. 29, 3175, 1964).

The present invention will be further explained by reference to the following examples directed to the preparation of the compounds of formula (I) and to the biological activity thereof.

EXAMPLE 1

Preparation of dimethyl 2(p-chlorophenoxy)-ethylphosphonate (Compound No. 1)

(Method adapted from G. M. Kosolapoff, Organic Reactions, Vol. 6, p. 273, 1951)

A mixture of 23.6 g (0.1 mol) of 2(p-chlorophenoxy)-ethyl bromide and 46 g (0.37 mol) of trimethylphosphite was refluxed at 115° C. for 30 hours. Distillation under reduced pressure gave 13.9 g (0.053 mol) of a white oil.

bp: 125°–126° C. (5.10$^{-2}$ mmHg)

yield: 53%

EXAMPLE 2

Diethyl 2(p-chlorophenoxy)-ethylphosphonate (Compound No. 3)

(Method adapted from G. M. Kosolapoff, see Example 1)

A mixture of 14 g (73.3 mmol) of 2(p-chlorophenoxy)-ethyl chloride (prepared according to the same method referred to in Example 1) and 36.5 g (220 mmol) of triethyl phosphite was refluxed at 160° for 84 hours. After the excess of triethyl phosphite was removed, the residue was distilled to give 13.6 g (46.5 mmol) of a white oil.

bp: 129°–131° C. (5.10$^{-2}$ mmHg)

yield: 63%

EXAMPLE 3

Diethyl 3(p-chlorophenoxy)-propylphosphonate (Compound No. 4)

(Method adapted from G. M. Kosolapoff, see Example 1)

A mixture of 50 g (0.20 mol) of 3(p-chlorophenoxy)-propylbromide (prepared according to the same method referred to in Example 1) and 77.4 g (0.47 mol)

of triethyl phosphite was refluxed at 160° for seven and a half hours. During this period the circulating water in the condenser was maintained at 50° by means of a thermoregulated bath to ensure the complete removal of the ethyl bromide evolved (bp: 38°). After the excess of triethyl phosphite was removed under reduced pressure, the residue was distilled under high vacuum to give 55 g (0.18 mol) of a white viscous oil.
bp: 135°–140° C. (5.10$^{-2}$ mmHg)
yield: 90%

EXAMPLE 4

3(p-chlorophenoxy)-propylphosphonic acid (Compound No. 7)

(Method adapted from G. M. Kosolapoff J. Am. Chem. Soc. 67, 2259, 1945)

A mixture of 10 g (32.6 mmol) of Compound 4 and 21 g of 37% hydrochloric acid was refluxed for 15 hours. After cooling, a white solid precipitated out. The acid solution was decanted and the solid dissolved in 100 ml ether. The ether solution was passed through a silicone-treated filter to remove water and was then evaporated to dryness. The solid residue was repeatedly recrystallized from an ether: acetone: petroleum ether (80:5:15) mixture to give 3.3 g (13 mmol) of white flaky crystals.
mp: 131°–132° C.
yield = 40%

For water-solubility purposes mainly, Compound 7 was transformed into its di-sodium salt, according to the following procedure: to 1.5 g (6 mmol) of Compound 7 dissolved in 12 ml of methanol was added a solution of 0.48 g (12 mmol) of sodium hydroxide in 6 ml 80% methanol. The mixture was evaporated to dryness and the white residue recrystallized in a water:ethanol 1:1 mixture. 1.8 g (100%) of the disodium salt of 3(p-chlorophenoxy)-propylphosphonic acid was thus recovered.

EXAMPLE 5

Diethyl 4(p-chlorophenyl)butylphosphonate (Compound No. 12)

A mixture of 12.38 g of 4(p-chlorophenyl)butyl bromide and 20 g of triethyl phosphite was refluxed at 160° for seven hours. During this period the circulating water in the condenser was maintained at 50° to allow the ethyl bromide to distill off. After removal of the excess of triethyl phosphite, distillation under reduced pressure gave 11.9 g (39 mmol) of a white viscous oil.
bp = 135°–138° C. (5.10$^{-2}$ mm Hg)
yield: 78%

EXAMPLE 6

4-Phenylbutylphosphonic acid (Compound No. 15)

A mixture of 5.4 g (20 mmol) of diethyl 4-phenylbutylphosphonate (Compound 11, synthesized exactly by the same method described in Example 5) and 14 g of 37% hydrochloric acid was refluxed for five hours. The excess of acid was removed under vacuum leaving an oil that slowly solidified Recrystallization from an ethanol:petroleum ether (40:60) mixture gave 1.7 g (8 mmol) of white crystals.
mp = 88°–90° C.
yield = 39%

TABLE I

PHYSICAL PROPERTIES OF COMPOUNDS (I)

| Compound No. | R | n | m | X | bp (°C./mm Hg) | mp (°C.) | IR spectra (cm$^{-1}$) |
|---|---|---|---|---|---|---|---|
| 1 | —PO$_3$Me$_2$ | 2 | 1 | p-Cl | 125–126 (5.10$^{-2}$) | | 2980–2940 (aliph. C—H) |
| 2 | —PO$_3$Me$_2$ | 3 | 1 | p-Cl | 127–129 (5.10$^{-2}$) | | 1420 (arom. C—C); 1240 |
| 3 | —PO$_3$Et$_2$ | 2 | 1 | p-Cl | 129–131 (5.10$^{-2}$) | | (P = 0; C - 0); 1060, |
| 4 | —PO$_3$Et$_2$ | 3 | 1 | p-Cl | 135–140 (5.10$^{-2}$) | | 1030, 940 (P—O—C), 830 |
| 5 | —PO$_3$Et$_2$ | 4 | 1 | p-Cl | 145–150 (5.10$^{-2}$) | | 660 (1,4-disubst. phenyl) |
| 6 | —PO$_3$H$_2$ | 2 | 1 | p-Cl | | 129–131 | 3400–3800 (P—O—H) |
| | | | | | | | 1500 (arom. C—C); |
| 7 | —PO$_3$H$_2$ | 3 | 1 | p-Cl | | 131–132 | 1250 (P = 0; C - 0); |
| | | | | | | | 1000, 960 (P—O—C), 830 |
| 8 | —PO$_3$H$_2$ | 4 | 1 | p-Cl | | 104–106 | |
| 9 | —PO$_3$Et$_2$ | 2 | 0 | H | 90–95 (5.10$^{-2}$) | | 2980–2940 (aliph. C—H) |
| 10 | —PO$_3$Et$_2$ | 3 | 0 | H | 113–115 (5.10$^{-2}$) | | 1420 (arom. C—C) |
| 11 | —PO$_3$Et$_2$ | 4 | 0 | H | 122–125 (5.10$^{-2}$) | | 1240 (P = 0) |
| 12 | —PO$_3$Et$_2$ | 4 | 0 | p-Cl | 135–138 (5.10$^{-2}$) | | 1030, 940 (P—O—C) |
| 13 | —PO$_3$H$_2$ | 2 | 0 | H | | 137–139° | 3800–3400 (P—O—H); |
| 14 | —PO$_3$H$_2$ | 3 | 0 | H | | 122–124° | 1500 (arom. C—C) |
| | | | | | | | 1250 (P = 0) |
| 15 | —PO$_3$H$_2$ | 4 | 0 | H | | 88–90° | 1000, 960 (P—O—C) |

EXAMPLE 7

Biological activity of compounds (I)

In order to observe the biological activity of the new compounds of formula (I), pharmacological screening tests were carried out. These initial results led the present inventor to examine in more detail the activity of these monophosphonates, and more particularly of Compound 4, in affecting a hypoglycemic response, changes in lipoprotein profiles, and clearance of cholesterol from various tissues.

Male Wistar rats (4-5/group) weighing 150 to 200 g were treated for 4 days with compound 4 or the respective vehicle. The lipid soluble monophosphonate was solubilized in corn oil and administered by gastric intubation (at a dosage of 50 mg/kg), corn oil alone being used as control. The rats were fastened overnight and sacrificed the 5th day by decapitation under light ether anesthesia. Blood samples were collected using E.D.-T.A. as anticoagulant. The livers, epididymal fat pads and aortas were weighted and stored at −20° C. until utilized for lipid extraction.

Methods

Hypoglycemic activity

Glucose concentration was determined by the enzymatic method of Werner, W., H. G. and Wielinger, (Z.

Analyt. Chem. 252, 224, 1970) (glucose oxidase-peroxidase) obtained from Boehringer Mannheim (nr 124036).

Atherosclerotic Index

Fresh plasma lipoproteins were stained with sudan-black and analysed by electrophoresis using polyacrylamide gels according to Frings, G. S. et al. (Clinical Chemistry, 17, 111, 1971). The separated high density lipoproteins (HDL), low density lipoproteins (LDL) and very low density lipoproteins (VLDL) were quantitated by densitometric tracings of the gels.

The values thus obtained were used to calculate the lipoprotein ratio $$\frac{HDL}{LDL + VLDL}.$$

According to G. J. Miller and N. E. Miller (Lancet 1, 16–19, 1975), as well as countless others, sufficient evidence has been presented to suggest that increased HDL levels are associated with decreased coronary risk and atherosclerosis.

Cholesterol removal from tissues

For this test, control and treated animals were previously given p.o. a cholesterol supplement of 160 mg/kg per day for two weeks prior to and during treatment with compound 4.

Lipids were extracted from livers and epididymal fat pads according to J. Folch et al (J. Biol. Chem. 226, 497, 1957) and the cholesterol content of the extracts was determined by the Liebermann-Burchard reaction (Chem. Ber. 18, 1803, 1885 and Chem. Ber. 61, 25, 1890).

Results

The results of the various tests realized as mentioned above are presented in the following Table II.

It can be seen from this Table II that Compound 4 significantly decreases blood glucose by 32%, increases the lipoprotein ratio HDL/LDL+VLDL by 108%, and decreases liver cholesterol by 18% and epididymal fat pad cholesterol by 46%, with regard to the control values.

Depending on the dosage and the vehicle used, changes in blood total lipids, free fatty acids, cholesterol, triglycerides and insulin were observed, further indicating that the compounds (I) according to the present invention have profound activities on lipid and carbohydrate metabolism.

It can be further pointed out, that compounds (I) produce a remarkable hypoglycemic activity and increase the quantity of circulating high density lipoproteins. In addition, these compounds (I) have the ability to clear cholesterol from various tissues even in the presence of exogenously added cholesterol to the diet.

Therefore, compounds of formula (I) according to the present investigation possess the potential use as hypoglycemic and/or antiatherogenic compounds.

Safe and effective amounts of phosphonate compound are prepared in sufficient amounts to produce a desirable effect at a reasonable benefit/risk ratio attendant with any medical treatment. Within the scope of acceptable and sound medical judgment, the dosage of phosphonate compound will vary with the particular condition being treated, the severity of the conditions, the duration of the treatment, and the specific phosphonate compound employed.

The phosphonates are prepared as pharmaceutically acceptable products which include all ingredients used in the compositions employed and are suitable for use in contact with the tissues of humans and animals without undue toxicity, irritation, allergic response commensurate with a reasonable benefit/risk ratio.

Preparation of the pharmaceutical compositions according to the present invention for oral unit dosage forms can be a mixture with a solid vehicule containing lactose, saccharose, sorbitol, mannitol, amidon, amylopectine, cellulose derivative, and/or gelatine which can be prepared with the lubricants such as magnesium stearate, calcium stearate, forms of "carbowax" and/or polyethylene glycol. It can be preferable in some cases to use a capsule, and the ingredients can then consist of a mixture containing concentrated sugar, arabic gum, talc, and/or titan bioxide.

In some cases particular phosphonates can be mixed in buffer solution, corn oil, olive oil, glycerol commercial fillers, and administered in a closed hard gelatin capsule, as drops, or sirop forms.

In addition, the phosphonates can be fabricated with "Imhausen H" to produce suitable suppositories.

For example, Compound 4 was compressed in tablet form with magnesium stearate 10% and amidon 25% to obtain a final concentration of about 50 to 250 mg active agent. In addition compounds of formula (I) can be used up in solution of drinking water or corn oil at concentrations between about 2 mg/ml and 100 mg/ml.

TABLE II

| | BIOLOGICAL ACTIVITY OF COMPOUNDS (I) | | | |
|---|---|---|---|---|
| | Plasma glucose (mg/100 ml) | Lipoprotein ratio HDL/LDL + VLDL | Liver cholesterol (mg/g tissue) | Epididymal fat pad cholesterol (mg/g tissue) |
| Control (corn oil) | 87 ± 3 | 2.61 | 3.4 ± 0.1 | 12.0 ± 2.9 |
| Cpd. 4 | 63 ± 4 | 5.44 | 2.8 ± 0.1 | 8.2 ± 0.5 |

I claim:
1. Monophosphonate compounds of formula (I),

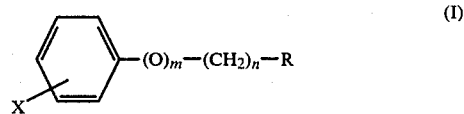
(I)

where R is —PO$_3$Me$_2$, —PO$_3$Et$_2$, —PO$_3$H$_2$ or —PO$_3$Na$_2$; X is an halogen; m is 0 or 1; and n is 2, 3, 4, 5 or 6.

2. Halogenophenoxy-alkylphosphonate compounds of formula (Ia) according to claim 1,

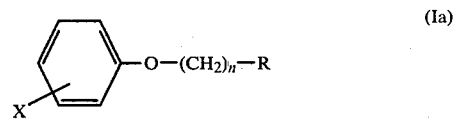
(Ia)

where R, n and X are as defined in claim 1.

3. Halogenophenyl-alkylphosphonate compounds of formula (Ib) according to claim 1,

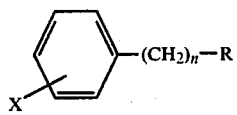

where R, n and X are as defined in claim 1.

4. Monophosphonate compounds of formula (I) according to one of the claims 1 to 3 in which X is a chlorine atom in p-position.

5. Hypoglycemic and/or antiatherogenic composition which comprises as active ingredient an effective amount of a monophosphonate compound of formula (I),

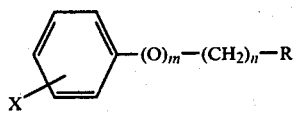

where R is $-PO_3Me_2$, $-PO_3Et_2$, $-PO_3H_2$ or $-PO_3Na_2$; X is a halogen; m is 0 or 1; and n is 0, 1, 2, 3, 4, 5 or 6.

6. Hypoglycemic and/or antiatherogenic composition which comprises as active ingredient an effective amount of halogenophenoxy-alkylphosphonate compound of formula (Ia),

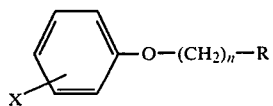

where R, n and X are as defined in claim 5.

7. Hypoglycemic and/or antiatherogenic composition which comprises as active ingredient an effective amound of a halogenophenyl-alkylphosphonate compound of formula (Ib),

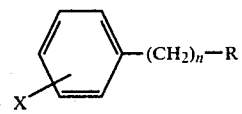

where R, n and X are as defined in claim 5.

8. Hypoglycemic and/or antiartherogenic composition according to one of the claims 5 to 7 in which X is a chlorine atom in p-position.

* * * * *